United States Patent
Gore et al.

(10) Patent No.: US 10,435,653 B1
(45) Date of Patent: *Oct. 8, 2019

(54) NATURAL EDIBLE CLEANING COMPOSITION

(71) Applicants: Jessica Adelle Gore, Plano, TX (US); Corby Lucious Frazier, Plano, TX (US)

(72) Inventors: Jessica Adelle Gore, Plano, TX (US); Corby Lucious Frazier, Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/973,389

(22) Filed: May 7, 2018

Related U.S. Application Data

(63) Continuation of application No. 15/350,820, filed on Nov. 14, 2016, now Pat. No. 9,963,663, which is a continuation of application No. 14/945,400, filed on Nov. 18, 2015, now Pat. No. 9,534,193.

(60) Provisional application No. 62/081,400, filed on Nov. 18, 2014.

(51) Int. Cl.
| | |
|---|---|
| C11D 3/04 | (2006.01) |
| C11D 3/382 | (2006.01) |
| C11D 7/26 | (2006.01) |
| C11D 7/44 | (2006.01) |
| A23L 3/3472 | (2006.01) |
| A23B 7/154 | (2006.01) |
| C11D 3/48 | (2006.01) |
| A01N 65/34 | (2009.01) |
| A01N 25/00 | (2006.01) |

(52) U.S. Cl.
CPC ............ *C11D 7/265* (2013.01); *A01N 25/002* (2013.01); *A01N 65/34* (2013.01); *A23B 7/154* (2013.01); *A23L 3/3472* (2013.01); *C11D 3/382* (2013.01); *C11D 3/48* (2013.01); *C11D 7/268* (2013.01); *C11D 7/44* (2013.01); *A23V 2002/00* (2013.01)

(58) Field of Classification Search
CPC .......... C11D 3/042; C11D 3/382; C11D 7/26; C11D 7/44; A23L 3/3472
See application file for complete search history.

(56) References Cited

U.S. PATENT DOCUMENTS

| | | | | |
|---|---|---|---|---|
| 5,652,011 A | * | 7/1997 | Heertje | A23D 7/0056 426/601 |
| 6,156,362 A | * | 12/2000 | Cirigliano | A23D 7/015 426/330.3 |
| 6,368,653 B1 | * | 4/2002 | Heertje | A23D 7/0056 426/601 |
| 8,206,761 B2 | | 6/2012 | Kutumian | |
| 8,338,347 B2 | | 12/2012 | Ibrahim et al. | |
| 8,741,827 B2 | | 6/2014 | Vyrostko et al. | |
| 9,534,193 B1 | * | 1/2017 | Gore | C11D 7/44 |
| 9,963,663 B1 | * | 5/2018 | Gore | C11D 7/44 |
| 2006/0286062 A1 | | 12/2006 | Schep et al. | |
| 2008/0311215 A1 | | 12/2008 | Grace | |
| 2010/0322976 A1 | * | 12/2010 | Sharma | A61K 36/33 424/278.1 |
| 2013/0143788 A1 | | 6/2013 | Baker et al. | |

FOREIGN PATENT DOCUMENTS

| | | |
|---|---|---|
| CA | 2513784 A1 | 11/2006 |
| CA | 2678909 A1 | 4/2011 |
| KR | 20040091969 A | 11/2004 |
| KR | 20120091813 A | 8/2012 |
| WO | WO2013066403 A1 | 6/2013 |
| WO | WO2017087559 A1 | 5/2017 |

OTHER PUBLICATIONS

European Search Report, PCT/US2016062338, dated Mar. 12, 2019.
PCT International Search Report and Written Opinion, PCT/US2016062338, dated Mar. 16, 2017.
Grenby T H Ed—Anese Monica et al., "Intense Sweeteners for the Food Industry: An Overview," Trends in Food Science and Technology, Elsevier Science Publishers, GB, vol. 2, No. 1, Jan. 1, 1991, pp. 2-06, XP000892985, ISSN: 0924-2244, DOI: 10.1016/0924-2244(91)90598-D, p. 4.

\* cited by examiner

*Primary Examiner* — Brian P Mruk
(74) *Attorney, Agent, or Firm* — Law Office of Sam Sokhansanj PLLC

(57) ABSTRACT

A cleaning solution, composition, and portable cleaner are provided that is all natural, safe, non-toxic, edible, antibacterial, anti-microbial, deodorizing, and further includes a pleasant fragrance and taste. In addition, the cleaning composition can be free from sugar, alcohol, surfactants, and other harmful or harsh ingredients. In addition, the cleaning composition allows for quick cleaning of any type of object that may be placed in the mouth, such as pacifiers, toys, candy, eating utensils, musical instruments, and mouthpieces, among others.

17 Claims, No Drawings

NATURAL EDIBLE CLEANING COMPOSITION

CROSS REFERENCE TO RELATED APPLICATIONS

This application is a continuation of and claims the benefit of U.S. Non-Provisional application Ser. No. 15/350,820 filed on Nov. 14, 2016 and issued as U.S. Pat. No. 9,963,663 on May 8, 2018, which is incorporated herein by reference in its entirety, which is a continuation of and claims the benefit of U.S. Non-Provisional application Ser. No. 14/945,400 filed on Nov. 18, 2015 and issued as U.S. Pat. No. 9,534,193 on Jan. 3, 2017, which is incorporated herein by reference in its entirety, which further claims the benefit of U.S. Provisional Application No. 62/081,400 filed on Nov. 18, 2014, which is incorporated herein by reference in its entirety.

BACKGROUND

This section is intended to introduce the reader to aspects of art that may be related to various aspects of the present disclosure described herein, which are described and/or claimed below. This discussion is believed to be helpful in providing the reader with background information to facilitate a better understanding of the various aspects of the present disclosure described herein. Accordingly, it should be understood that these statements are to be read in this light, and not as admissions of prior art.

There are numerous conventional cleaning products commercially available on the market. However, these conventional cleaning products can generally only be used in a limited number of cleaning applications and can include toxic and hazardous substances and compositions. Unless the cleaning solution is safe for washing or cleaning fruits, vegetables, and other foods, then they typically do not have formulations or compositions that are edible and safe for possible human consumption. Further, conventional multi-purpose cleaning solutions on the market do not currently have an all-natural ingredient composition. Further, most are not available in quick and ready-to go type of packaging that the user may use at any time or place.

In general, a dirty or soiled object that needs to be placed in the mouth (i.e. teeth retainers, mouth/lip guards, foods, etc.) will require cleaning or disinfecting. Hence, a user will need to manually wash the object with a soap/detergent and running water. This is because most conventional all-purpose cleaners on the market are not edible and are not pre-packaged in a portable container that the user can carry on him or her person. Consequently, this can become a cumbersome process if the user does not readily have access to such a cleaning solution. Further, since these cleaning products are not edible and are toxic, the user will need to completely rinse the object having the cleaning solution on it with running water prior to placing it in his or her mouth.

Hence, what is needed is a cleaning solution, composition, and portable cleaner that is comprised of all-natural ingredients that are safe, non-toxic, edible, anti-bacterial, anti-microbial, and further include a pleasant fragrance and taste that a user can use at any time and in any situation that requires quick and safe cleaning.

BRIEF SUMMARY

In one aspect of the disclosure described herein, a cleaning solution, composition, and portable cleaner are provided that is all natural, safe, non-toxic, edible, anti-bacterial, anti-microbial, deodorizing, and further includes a pleasant fragrance and taste. In addition, the cleaning composition can be free from sugar, alcohol, parabens, surfactants, and other harmful ingredients. In addition, the cleaning composition of the disclosure described herein allows for quick cleaning of any type of object that may be placed in the mouth, such as pacifiers, toys, candy, utensils, musical instruments, and mouth-pieces, among others.

In another aspect of the disclosure described herein, a multi-purpose cleaning composition is disclosed that includes an edible (non-toxic) and pathogen disinfecting formulation further comprising apple cider vinegar and grapefruit seed extract. The apple cider vinegar can be further comprised of approximately 0.5% wt. or volume to approximately 20% wt. or volume of the formulation, or about 1% to 10% by volume of the formulation. In addition, the apple cider vinegar can also be further comprised of about 3% wt. of the formulation. The apple cider vinegar can also be further comprised of 3.25% wt. of the formulation. The grapefruit seed extract can be further comprised of approximately 0.05% wt. to 5% wt. of the formulation.

The grapefruit seed extract can also be further comprised of about 1% wt. of the formulation. The grapefruit seed extract can also comprise 1.25% wt. of the formulation. The formulation can further include *Stevia* Leaf Extract and one or more flavoring ingredients. The cleaning composition can also include Reb-A, sodium benzoate, and potassium sorbate. Here, cleaning composition is safe, non-toxic, and edible and can be dispensed on to an object or surface that is to be orally used (within a user's mouth) or administered orally without requiring rinsing or wiping of the cleaning composition residue prior to oral administration. For example, such objects may include teeth retainers, mouth/lip guards, eating utensils, baby or toddler toys or articles (i.e. teething articles), foods (i.e. fruits, vegetables, etc.), and musical instruments (i.e. brass/wind instruments), among others.

The above summary is not intended to describe each and every disclosed embodiment or every implementation of the disclosure. The Description that follows more particularly exemplifies the various illustrative embodiments.

DETAILED DESCRIPTION

In the Brief Summary of the present disclosure above and in the Detailed Description of the disclosure described herein, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

TABLE 1 illustrates a table of ingredients for one non-limiting embodiment of the cleaning composition having a cherry flavor. Here, the ingredients can include but are not limited to: water, apple cider vinegar (ACV), *Stevia* leaf extract, Reb-A, Sodium Benzoate, Potassium Sorbate, Grapefruit Seed Extract, FCI natural cherry flavoring, FCI lemon natural liquid, and citric acid. Here, the active ingredients can include primarily ACV, grapefruit seed extract, and citric acid. In one embodiment, water can comprise approximately 90% or 91.3% by weight or volume of the total composition. However, in other embodiments, water may comprise approximately 10% up to and including 80% by weight or volume of the total composition. Here, ACV can comprise approximately 3% or 3.25% by weight or volume of the total composition. In other embodiments, ACV can comprise from 0.05% up to and including 50% by weight or volume of the total composition. In the current embodiment, grapefruit seed extract can comprise of approximately 0.125% by weight or volume of the total composition. In other embodiments, grapefruit seed extract may include from 0.05% up to and including 90% by weight or volume of the total composition.

Still referring to TABLE 1, citric acid may comprise of approximately 2.5% by weight or volume of the total composition. However, in other embodiments, citric acid may comprise of 0.05% up to and including 90% by weight or volume of the total composition. Also, *Stevia* leaf extract and Reb-A each may comprise approximately 0.06% or 0.063% by weight or volume of the total composition. Further, Sodium Benzoate and Potassium Sorbet each may comprise approximately 0.1% by weight or volume of the total composition.

Still referring to TABLE 1, the cleaning composition can further include a natural or artificial flavoring such as cherry or natural lemon, alone or in combination, which can comprise approximately 2.5% by weight or volume of the total composition. However, in other embodiments, flavoring can comprise from 0.05% up to and including 25% by weight or volume of the total composition. In addition, it is contemplated within the scope of the invention that any type of flavoring can be added in addition to or in lieu of cherry, including but not limited to: sweet, sour, bitter, salty, umami flavoring, mint, orange, chocolate, vanilla, among others. Further, the flavoring may be natural flavoring substances, nature-identical flavoring substances, and/or artificial flavoring substances.

Also, in other embodiments, the cleaning composition may also have a low level of foaming to improve cleaning and/or washing of the object for which it is being applied.

TABLE 1

Cherry Flavor

| Actual mg | Ingredients | 1 Kilo | % of Formula | Kgs |
|---|---|---|---|---|
| 7304 | Water | 913.00 | 91.3% | 0.9130 |
| 260 | ACV | 32.50 | 3.25% | 0.0325 |
| 5 | Stevia Leaf Extract | 0.63 | 0.063% | 0.0006 |
| 5 | Reb-A | 0.63 | 0.063% | 0.0006 |
| 8 | Sodium Benzoate | 1.00 | 0.1% | 0.0010 |
| 8 | Potassium Sorbate | 1.00 | 0.1% | 0.0010 |
| 10 | Grapefruit Seed Extract | 1.25 | 0.125% | 0.0013 |
| 130 | FCI Natural Cherry | 16.25 | 1.625% | 0.0163 |

TABLE 1-continued

Cherry Flavor

| Actual mg | Ingredients | 1 Kilo | % of Formula | Kgs |
|---|---|---|---|---|
| 70 | FCI Lemon Natural Liquid | 8.75 | 0.875% | 0.0088 |
| 200 | Citric Acid | 25.00 | 2.5% | 0.0250 |

TABLE 2 illustrates a table of ingredients for another non-limiting embodiment of the cleaning composition having a cherry flavor with alternative ingredients, such as not including grapefruit seed extract. Here, the ingredients can include but are not limited to: water, ACV, *Stevia* leaf extract, Reb-A, FCI natural cherry, FCI lemon natural liquid, and citric acid. Here, the active ingredients can include primarily ACV and citric acid.

TABLE 2

Cherry Flavor-2 (Alternative)

| Actual mg | Ingredients | 1 Kilo | % of Formula | Kgs |
|---|---|---|---|---|
| 7330 | Water | 916.25 | 91.625% | 0.9165 |
| 260 | ACV | 32.50 | 3.25% | 0.0325 |
| 5 | Stevia Leaf Extract | 0.63 | 0.063% | 0.0006 |
| 5 | Reb-A | 0.63 | 0.063% | 0.0006 |
| 130 | FCI Natural Cherry | 16.25 | 1.625% | 0.0163 |
| 70 | FCI Lemon Natural Liquid | 8.75 | 0.875% | 0.0088 |
| 200 | Citric Acid | 25.00 | 2.5% | 0.0250 |

TABLE 3 illustrates a table of ingredients for another non-limiting embodiment of the cleaning formulation having a Pina Colada flavor. Here, the ingredients can include but are not limited to: water, ACV, *Stevia* leaf extract, Reb-A, Sodium Benzoate, Potassium Sorbate, Grapefruit Seed Extract, FCI Pina Colada flavoring, and citric acid. Further, the active ingredients can include primarily ACV, grapefruit seed extract, and citric acid.

TABLE 3

Pina Colada Flavor

| Actual mg | Ingredients | 1 Kilo | % of Formula | Kgs |
|---|---|---|---|---|
| 7304 | Water | 913.00 | 91.3% | 0.9130 |
| 260 | ACV | 32.50 | 3.25% | 0.0325 |
| 5 | Stevia Leaf Extract | 0.63 | 0.063% | 0.0006 |
| 5 | Reb-A | 0.63 | 0.063% | 0.0006 |
| 8 | Sodium Benzoate | 1.00 | 0.1% | 0.0010 |
| 8 | Potassium Sorbate | 1.00 | 0.1% | 0.0010 |
| 10 | Grapefruit Seed Extract | 1.25 | 0.125% | 0.0013 |
| 200 | FCI Pina Colada | 25.00 | 2.5%% | 0.0250 |
| 70 | Citric Acid | 25.00 | 0.875% | 0.0088 |

TABLE 4 illustrates a table of ingredients for another non-limiting embodiment of the cleaning composition having a Pina Colada flavor having alternative ingredients, such as not including grapefruit seed extract. Here, the ingredients can include but are not limited to: Water, ACV, *Stevia* leaf extract, Reb-A, FCI Pina Colada, and citric acid. Further, the active ingredients can include primarily ACV and citric acid.

TABLE 4

| Pina Colada-2 (Alternative) | | | | |
|---|---|---|---|---|
| Actual mg | Ingredients | 1 Kilo | % of Formula | Kgs |
| 7330 | Water | 916.25 | 91.625% | 0.9165 |
| 260 | ACV | 32.50 | 3.25% | 0.0325 |
| 5 | Stevie Leaf Extract | 0.63 | 0.063% | 0.0006 |
| 5 | Reb-A | 0.63 | 0.063% | 0.0006 |
| 130 | FCI Pine Colada | 25.00 | 2.5% | 0.0250 |
| 200 | Citric Acid | 25.00 | 2.5% | 0.0250 |

The natural edible cleaning composition of the disclosure described herein was tested in one sample experiment. In particular, a log reduction/time kill test was used to determine the effectiveness of a product at reducing a specific microorganism population. Here, the organisms included *Escherichia coli, Pseudomonas aeruginosa, Staphylococcus aureus*, and *Klebsiella pneumonia*. Here, the organisms were prepared by inoculating the surface of tryptic soy agar slants. The microorganisms were incubated at 32.5±2.5° C. for 24 hours.

Following the incubation period the slants were washed with sterile Phosphate Buffered Saline (PBS) to harvest the microorganisms. The microbial suspension was adjusted to approximately $10^7$ colony forming units (CFU) per mL and labeled as the stock suspension. At the time intervals of 30 seconds, 1 minute, and 5 minutes, 1.0 mL from the inoculated test product was taken and placed into 9.0 mL of neutralizing broth (1:10 dilution). Additional 1:10 serial dilutions were prepared using neutralizing broth to achieve 1:100 and 1:1000 dilutions. One milliliter from each dilution was plated in duplicate and melted tryptic soy agar with polysorbate 80 and lecithin was added as the growth medium for the organisms. The plates were incubated at 35±2° C. for a minimum of 48 hours. The same procedure was repeated for the PBS control. After the incubation period, all plates were counted to determine the number of microorganisms remaining at each time point. The experimental results are illustrated in TABLE 5, TABLE 6, TABLE 7, and TABLE 8 for each microorganism using any of the aforementioned formulations of the disclosure described herein.

TABLE 5

| *Escherichia coli* | | | | | | |
|---|---|---|---|---|---|---|
| EXPOSURE TIME | CONCENTRATION OF ORGANISM (CFU/mL) | | % REDUCTION | | LOG REDUCTION | |
| | CONTROL | PRODUCT | CONTROL | PRODUCT | CONTROL | PRODUCT |
| Initial | 1.5E+05 | 1.5E+05 | N/A | N/A | N/A | N/A |
| 30 sec. | 2.5E+05 | 1.7E+05 | −66.7 | −13.3 | −0.2 | 0.1 |
| 1 min. | 2.3E+05 | 7.6E+04 | −53.3 | 49.3 | −0.2 | 0.3 |
| 5 min. | 1.8E+05 | <10 | −20.0 | >99.9 | −0.1 | 4.2 |

TABLE 6

| *Pseudomonas aeruginosa* | | | | | | |
|---|---|---|---|---|---|---|
| EXPOSURE TIME | CONCENTRATION OF ORGANISM (CFU/mL) | | % REDUCTION | | LOG REDUCTION | |
| | CONTROL | PRODUCT | CONTROL | PRODUCT | CONTROL | PRODUCT |
| Initial | 3.5E+05 | 3.5E+05 | N/A | N/A | N/A | N/A |
| 30 sec. | 3.1E+05 | <10 | 11.4 | >99.9 | 0.1 | 4.5 |
| 1 min. | 3.1E+05 | <10 | 11.4 | >99.9 | 0.1 | 4.5 |
| 5 min. | 3.7E+05 | <10 | −5.7 | >99.9 | 0.0 | 4.5 |

TABLE 7

| *Staphylococcus aureus* | | | | | | |
|---|---|---|---|---|---|---|
| EXPOSURE TIME | CONCENTRATION OF ORGANISM (CFU/mL) | | % REDUCTION | | LOG REDUCTION | |
| | CONTROL | PRODUCT | CONTROL | PRODUCT | CONTROL | PRODUCT |
| Initial | 1.1E+05 | 1.1E+05 | N/A | N/A | N/A | N/A |
| 30 sec. | 1.9E+05 | 1.2E+05 | −72.7 | −9.1 | −0.2 | 0.0 |
| 1 min. | 1.6E+05 | 1.5E+04 | −45.5 | 86.4 | −0.2 | 0.9 |
| 5 min. | 1.8E+05 | <10 | −63.6 | >99.9 | −0.2 | 4.0 |

TABLE 8

Klebsiella pneumonia

| EXPO-SURE TIME | CONCENTRATION OF ORGANISM (CFU/mL) | | % REDUCTION | | LOG REDUCTION | |
|---|---|---|---|---|---|---|
| | CONTROL | PRODUCT | CONTROL | PRODUCT | CONTROL | PRODUCT |
| Initial | 3.1E+05 | 3.1E+05 | N/A | N/A | N/A | N/A |
| 30 sec. | 5.1E+05 | 1.1E+04 | −64.5 | 96.5 | −0.2 | 1.4 |
| 1 min. | 4.4E+05 | 3.5E+02 | −41.9 | 99.9 | −0.2 | 2.9 |
| 5 min. | 3.9E+05 | <10 | −25.8 | >99.9 | −0.1 | 4.5 |

Still referring to the experiment and the results presented in TABLES 5-8, the concentration of each microorganism for the control and product is listed for each interval. Here, these numbers are expressed in terms of scientific notation. The next heading represents the "Log Reduction" information for each time point. The calculation is used to express the change (reduction or increase) of the microorganism population relative to a starting inoculum. The Log 10 reduction is calculated as follows: Log 10 (initial count)−Log 10 (x time interval)=Log 10 reduction. Here, The minimum bactericidal concentration is defined as 3 log reduction from the initial inoculum. The natural edible cleaning composition of the disclosure described herein did achieve more than 3 log reduction at the 30 seconds, 1 minute, and 5 minute time intervals for *Pseudomonas aeruginosa* (TABLE 6). In addition, the disclosure described herein did achieve 3 log reduction for *Escherichia coli* (TABLE 5), *Staphylococcus aureus* (TABLE 7) and *Klebsiella pneumonia* (TABLE 8) at around the 5 minute time interval.

In one embodiment, the cleaning composition of the disclosure described herein can be pre-packaged within a spray dispensing container. Here, the spray dispenser can be an 8 mL bottle storing and dispensing the cleaning composition of the disclosure described herein. Further, the spray dispenser can have a removable top with a hook for securing it to any part of clothing or article of clothing, such as pockets, belt loops, etc. Further, the spray dispenser is portable and be be placed within any type of pocket, purse, bag, or wallet. In addition, in other embodiments, the cap may include any type of fastener, such as cam and spring buckles, carabiners, footman loops, spring pins, clamps, hooks, mini carabiner, ratchet buckles, and/or snap hooks, among others. In addition, it may also have any adhesive or hook and loop (Velcro®) fastener. Also, it may be coupled to any other object, such as a key chain or key ring. Further, it is contemplated within the scope of the invention that the cleaning composition dispenser may also be of any size not limited to an 8 mL bottle, such as from 1 mL bottle up to and including to a 3 Liter bottle. In addition, the bottle may have any type of dispensing means, such as an open top, pourer, pop-top, push-down dispenser, horizontal or vertical sprayer, and/or any type of liquid atomizer.

A method of application of the edible cleaning composition of the disclosure described herein may be to immediately, or within 1-60 seconds (or any time period), pump one to ten sprays of the cleaning composition onto one or more surfaces of an object to be cleaned. The cleaning composition residue may then be wiped or dried off of the object. Alternatively, the cleaning composition may self-dry within 1 second up to and including 1 hour. In other embodiments, the object to be cleaned may also be dipped or soaked within the cleaning composition for a pre-determined period of time. Here, the cleaning composition of the disclosure described herein can be safely edible in limited or trace amounts. For example, in one embodiment, if a eating utensil or food item to be cleaned is sprayed with the cleaning composition, the utensil may be used (i.e. placed in mouth) and food item consumed without rinsing or wiping off the cleaning composition or its residue. Here, the various flavoring of the cleaning composition assists with masking any unwanted tastes or smells from the aforementioned active ingredients of the cleaning composition, thereby providing a pleasant taste if limited or trace amounts of the cleaning composition is tasted, eaten, consumed, or administered orally.

According to a further aspect of the cleaning composition of the disclosure described herein, there is provided a means of destroying bacteria and/or inhibiting the ability of bacteria and/or viruses to replicate when said bacteria and/or viruses are present on a surface, the means comprising the application of a composition to said surface wherein the composition is configured to rupture the phospholipid membrane of the bacteria or virus or encapsulate the bacterial or viral structures and prevent the replication of their genetic material. These advantages allow for rapid decontamination of a surface.

The cleaning composition of the disclosure described herein may further include in one or more embodiments any type of surfactants. Here, the surfactant contained within the composition of the invention is any organic compound that contains at least one hydrophobic functional group and one hydrophilic functional group (i.e., an amphiphilic compound). The surfactants may be ionic or non-ionic in nature. Examples of surfactants include, but are not limited to, sodium dodecylsulfate, sodium laureth sulfate, sodium dodecylbenzenesulfonate, alkyl poly(ethylene oxide), and cetyl alcohol. Other surfactants are well known in the art and are equally suitable.

Further, the cleaning composition of the disclosure described herein may further in one or more embodiments any type of alkaline base. Here, the alkaline base contained within the composition of the invention is the basic salt of any alkali metal or alkaline earth metal. Examples of suitable alkaline bases include, but are not limited to, sodium carbonate, sodium bicarbonate, sodium hydroxide, potassium carbonate, potassium bicarbonate, potassium hydroxide, calcium carbonate, and magnesium hydroxide. Other alkaline bases are well known in the art and are equally suitable. It should be noted that the alkaline base need not be soluble in water.

The cleaning composition of the disclosure described herein may further include in one or embodiments one or more drying agents. Here, The drying agent contained within the composition of the invention is any agent that has the ability to react with, absorb, or adsorb either liquid water or water vapor. Drying agents are also commonly referred to as "desiccants" in the art. Examples of suitable drying agents include, but are not limited to, sodium sulfate, magnesium sulfate, and silica gel. Other drying agents are well known in the art and are equally suitable. Without introducing any limitations to the scope of this invention, it should be noted that drying agents derived from the alkali metals (e.g., sodium sulfate) are preferred over drying agents derived from the alkaline earth metals (e.g., magnesium sulfate) because the latter has a tendency to bind to the sequestering agent. This can be remedied, however, by using an excess of the sequestering agent when a drying agent derived from an alkaline earth metal is employed.

The cleaning composition of the disclosure described herein may further include in one or more embodiments indicator dyes or color changing on contact. Here, the indicator dye contained within the composition of the invention can be any compound that exhibits a colorimetric response when exposed to a surface. This calorimetric response may include, but is not limited to, the change from one color to another, or the disappearance of a color. Suitable indicator dyes include, but are not limited to, FD&C Blue No. 1, FD&C Blue No. 2, FD&C Green No. 3, FD&C Red No. 40, FD&C Red No. 3, FD&C Yellow No. 5, FD&C Yellow No. 6. Other indicator dyes are well known in the art and are equally suitable.

Further, the cleaning composition of the disclosure described herein may also include a fragrance or aroma. The fragrant substance contained within the composition of the invention may be any substance that imparts a pleasant odor to the cleaning composition either within a container or when dispensed on a surface. The fragrance may be used to mask any type of odor on a surface or from other ingredients within the composition. Suitable fragrances include, but are not limited to, essential oils, such as peppermint oil, and any other natural or synthetic fragrance.

Further, the cleaning composition of the disclosure described herein may also include additional disinfecting ingredients, including but not limited to: hydrogen peroxide, alcohols, white vinegar, borax, liquid soap, tea tree oil (*Melaleuca*), and baking soda, among others.

The cleaning composition of the disclosure described herein may also include any percent volume weight (0.05% up to 95%) of one or more of: water, natural and artificial flavors, apple cider vinegar, glycerin, grapefruit seed extract, oat kernel extract, acas fruit extract, goji fruit extract, none fruit extract, *Echinacea anguvstifolia* extract, *Echinacea purpurea* extract, green tea leaf extract, potassium sorbate, sodium benzoate, sodium citatrate, vitamins A, B, C, D, E, and organic *Stevia* extract, in one or more combinations.

From the foregoing it will be seen that the disclosure described herein is one well adapted to attain all ends and objectives herein-above set forth, together with the other advantages which are obvious and which are inherent to the disclosure described herein.

Since many possible embodiments may be made of the disclosure described herein without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the disclosure described herein is not limited to the specific forms or arrangement of parts described herein, except insofar as such limitations are included in the following claims. Further, it will be understood that certain features and sub-combinations are of utility and may be employed without reference to other features and sub-combinations.

What is claimed is:

1. A cleaning formulation comprising:
   apple cider vinegar;
   *Stevia* leaf extract; and
   a preservative comprised of sodium benzoate or potassium sorbate.

2. The cleaning formulation of claim 1, wherein the apple cider vinegar is further comprised of approximately 1% wt. to approximately 20% wt. of the formulation.

3. The cleaning formulation of claim 1, wherein the sodium benzoate is comprised of at least about 0.1% wt. of the formulation.

4. The cleaning formulation of claim 1, wherein the potassium sorbate is comprised of at least about 0.1% wt. of the formulation.

5. The cleaning formulation of claim 1, further comprising a flavoring ingredient.

6. The cleaning formulation of claim 5, wherein the flavoring ingredient comprises at least about 1% wt. of the formulation.

7. The cleaning formulation of claim 1, further comprising water of approximately 90% wt. of the formulation.

8. A cleaning composition, comprising:
   apple cider vinegar;
   *Stevia* leaf extract;
   a preservative; and
   a flavoring ingredient.

9. The cleaning composition of claim 8, wherein the preservative is further comprised of sodium benzoate.

10. The cleaning composition of claim 9, wherein the sodium benzoate is comprised of at least about 0.1% wt. of the composition.

11. The cleaning composition of claim 8, wherein the preservative is further comprised of potassium sorbate.

12. The cleaning composition of claim 11, wherein the potassium sorbate is comprised of at least about 0.1% wt. of the formulation.

13. A cleaning formulation, comprising:
    apple cider vinegar;
    *Stevia* leaf extract; and
    a preservative.

14. The cleaning formulation of claim 13, wherein the apple cider vinegar is further comprised of approximately 1% wt. to approximately 20% wt. of the formulation.

15. The cleaning formulation of claim 8, wherein the preservative is comprised of sodium benzoate, and wherein the sodium benzoate is comprised of at least about 0.1% wt. of the formulation.

16. The cleaning formulation of claim 8, wherein the preservative is comprised of potassium sorbate, and wherein the potassium sorbate is comprised of at least about 0.1% wt. of the formulation.

17. The cleaning formulation of claim 13, further comprising a flavoring ingredient.

* * * * *